United States Patent [19]

Rabilloud et al.

[11] 4,147,728
[45] Apr. 3, 1979

[54] DISUBSTITUTED META-TERPHENYL COMPOUNDS AND RESULTING POLYMERS

[75] Inventors: Guy Rabilloud; Bernard Sillion, both of Grenoble, France

[73] Assignee: Institut Francais du Petrole, Rueil-Malmaison, France

[21] Appl. No.: 533,822

[22] Filed: Dec. 18, 1974

[30] Foreign Application Priority Data

Dec. 19, 1973 [FR] France .................................. 73 45637

[51] Int. Cl.$^2$ .............................................. C07C 49/78
[52] U.S. Cl. ................................ 260/590 D; 260/591; 528/245; 528/229
[58] Field of Search ......................... 260/590 R, 590 D

[56] References Cited

PUBLICATIONS

Siegrist et al., Helvetica Chimica Acta, vol. 52, pp. 2521-2554.
Goodman et al., J.A.C.S., vol. 60, pp. 2155-2157, (1938).

*Primary Examiner*—James O. Thomas, Jr.
*Assistant Examiner*—James H. Reamer
*Attorney, Agent, or Firm*—Millen & White

[57] ABSTRACT

New tetracarbonyl compounds of the formulae:

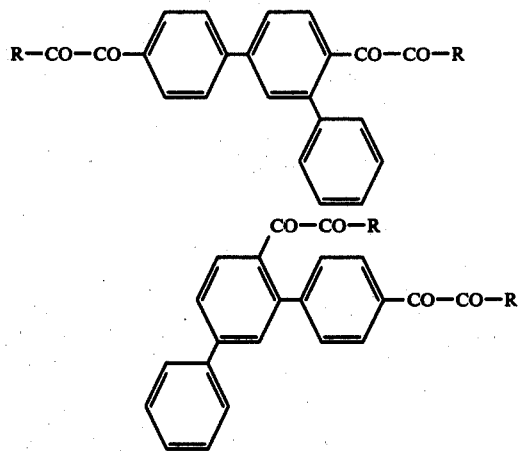

where R is a hydrogen atom, an alkyl radical or an aryl radical. The invention also contemplates the thermostable polymers obtained by reacting an aromatic tetraamine with at least one of the above tetracarbonyl compounds.

4 Claims, No Drawings

DISUBSTITUTED META-TERPHENYL COMPOUNDS AND RESULTING POLYMERS

This invention concerns new disubstituted meta-terphenyl compounds, the synthesis of these compounds and their use for preparing thermostable heterocyclic polymers.

It is known that compounds having aromatic rings have, as a rule, a very good thermal stability and a good resistance to oxidation. It is thus advantageous to use these compounds for preparing thermostable polymers, such as polyquinoxalines; but, although these polymers are known for their good stability to heat, oxidation or hydrolysis, they have the inconvenience of a poor solubility in organic solvents and also infusibility, so that they cannot be processed easily. It has been proposed to improve the solubility of these polymers and to increase their thermoplasticity by introducing ether, ketone, methylene, sulfide or sulfone linkages into their macromolecular chain. However increasing the number of these linkages strongly reduces the resistance of the polymers to oxidation above 300° C.

We have now discovered that it is possible to prepare new meta-terphenyl derivatives convenient for manufacturing thermostable polymers having an increased solubility in organic solvents and a high resistance to oxidation.

We have now found that a substituent could be introduced on the central ring of meta-terphenyl of the formula:

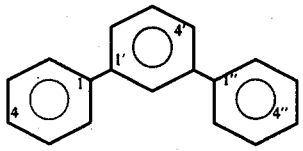

and a second substituent on one of the side rings, thereby forming disubstituted compounds having a pending phenyl ring.

One object of the invention is to produce new disubstituted dissymetric m-terphenyl compounds, particularly bis-α-ketoaldehydes and bis-α-diketones.

Another object of the invention is to prepare thermostable heterocyclic polymers, particularly polyquinoxalines and polypyrazinoquinoxalines, by means of these compounds.

The compounds according to the invention are tetracarbonyl compounds of the general formulae:

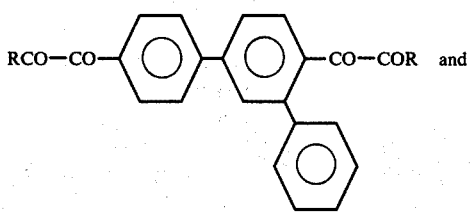
(1)

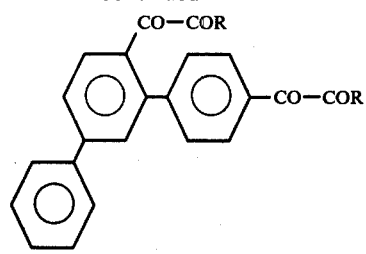
(2)

in which R is a hydrogen atom, an alkyl radical or an aryl radical, preferably methyl or phenyl. According to the invention, these compounds may be used individually or in admixture, or again as mixtures with minor proportions preferably not more than 30 molar percent of other isomeric compounds of the general formulae:

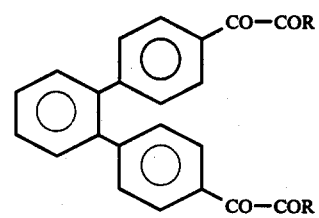
(3)

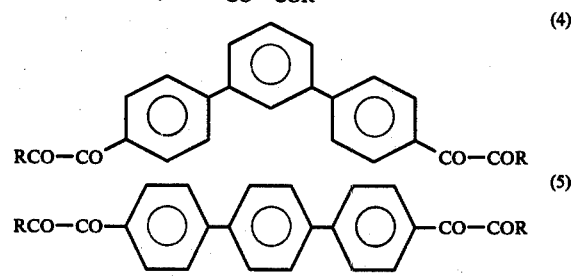
(4)

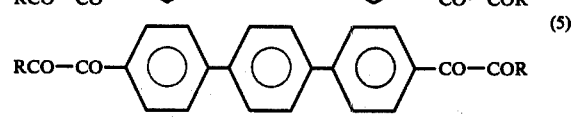
(5)

in which R is defined as above.

The synthesis of the tetracarbonyl compounds according to the invention is usually carried out in 2 steps. In all cases, the first step consists of acylating m-terphenyl under well defined conditions, to introduce, in a major proportion, a first substituent at the 4' position of the central ring of m-terphenyl. The reaction product is chiefly a 4'-acyl m-terphenyl of the general formula:

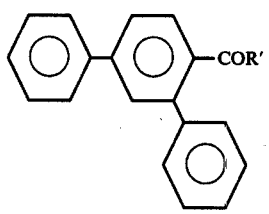
(6)

where R' is a monovalent hydrocarbon radical, for example, a methyl, ethyl or benzyl radical or a monovalent halohydrocarbon radical, for example, a chloromethyl, bromomethyl, dichloromethyl, dibromomethyl, phenylchloromethyl or phenyldichloromethyl radical, depending on the acylation agent.

The compound of the formula (6) is not usually isolated and the acylation reaction is continued, in order to introduce a second substituent in a 4 or 4" position of the side rings of m-terphenyl. The resulting new compounds have the general formulae:

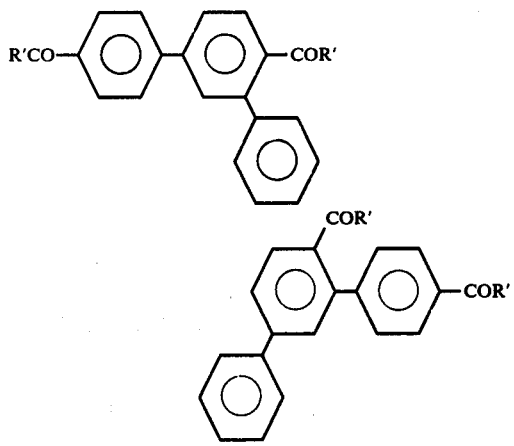

(7)

(8)

where R' is defined as above.

Under the conventional conditions of the Friedel and Crafts reaction, acylation, for example acetylation, of m-terphenyl normally yields 4-acetyl m-terphenyl and 4,4"-diacetyl m-terphenyl (GOODMAN AND LOWY, J. Amer. Chem. Soc. (1938), 60, 2155). We have now discovered that 4' acetyl m-terphenyl and 4,4'- and/or 4',4"-diacetyl m-terphenyl could be obtained in major proportion, provided that the solvent, the reaction temperature and the order of introduction of the reactants are conveniently selected.

According to a specific embodiment, m-terphenyl is subjected to the Friedel and Crafts reaction, at low temperature, preferably between −80° C. and 80° C., in the presence of a solvent, a catalyst and an acylation agent. The reactants are introduced in such an order as to first react the acylation agent with the catalyst to form a complex, known as the PERRIER complex, which is thereafter reacted with m-terphenyl.

The acylation agents used according to the invention comprise the carboxylic acid halides, preferably the chlorides and bromides, for example: acetyl chloride, acetyl bromide, chloracetyl chloride, dichloracetyl chloride, phenylacetyl chloride or phenylglyoxyloyl chloride. The carboxylic acids as such and the anhydrides or lower alkyl esters of these acids may also be used (lower alkyl = 1–6 carbon atoms).

Anhydrous LEWIS acids, also called Friedel and Crafts catalysts, for example aluminum chloride, aluminum bromide, boron trifluoride, ferric chloride and bromide, zinc chloride, stannic chloride, antimony pentachloride, indium trichloride, and polyphosphoric acid, are effective condensation catalysts.

The reaction is usually carried out in solution or in suspension in a relatively inert substance such as nitrobenzene, carbon sulfide, petroleum ether, hexane, tetrachlorethane or methylene chloride.

We have now found that the acylation could be performed specifically on the 4,4' and/or 4',4" positions by adding the acylation agent to a substantially equimolecular proportion of the catalyst in one of the solvents mentioned above, at a temperature of from −80° C. to 20° C., preferably from −30° C. to 0° C. These two reactants form a complex of relative stability at low temperature, to which m-terphenyl is quickly added, either in solid state or as a solution in the reaction solvent, the temperature being maintained below 20° C. and preferably at −30° C. to 0° C. during the addition. After a reaction time at low temperature which may range from a few minutes to several hours, the temperature of the mixture is allowed to increase to room temperature or to a higher temperature, preferably 10°–80° C., for a few hours. The reaction products are then isolated, according to a conventional technique, after hydrolysis of the reaction medium.

The compounds of the formulae (7) and (8) are the major products of the acylation reaction and may be obtained in the pure or commingled state. However they can also be obtained, according to the invention, in admixture with a minor proportion of other ortho-, meta- or para-terphenyl diacyl compounds of the general formulae:

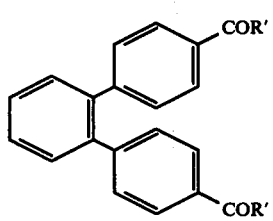

(9)

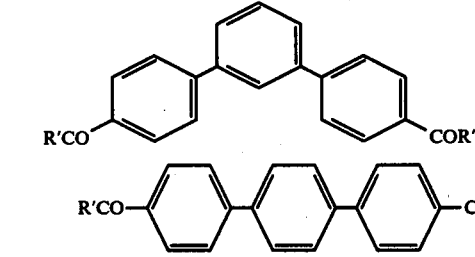

(10)

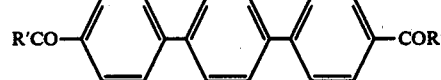

(11)

in which R' is defined as above.

By acylation of pure m-terphenyl we obtain in addition to the compounds of the formulae (7) and (8), amounts of 4,4'-diacyl m-terphenyl of the formula (10) and of 4,4"-diacyl p-terphenyl of the formula (11), the latter resulting from the isomerization of m-terphenyl to p-terphenyl by means of the Friedel and Crafts catalyst. The compounds of the formulae (9), (10) and (11) are formed at the same time as the compounds of the formulae (7) and (8), provided the acylation is carried out with so-called "technical" m-terphenyl which always contains variable proportions of ortho- and para-terphenyl. It is, however, preferable that the proportion of the isomers of the formulae (9), (10) and (11) be as low as possible and not in excess of 20 to 30 moles per each 80 to 70 moles of the compounds of formulae (7) and (8).

The diacyl compounds of the formulae (7) and (8), as well as the compounds of the formulae (9), (10) and (11), when present, are converted, during the second step, to tetracarbonyl compounds of the general formulae (1) and (2) and possibly (3), (4) and (5), as above.

However, the diacyl compounds of the formulae (9) and (11) are preferably eliminated, for example, by fractionated re-crystallization. We thus obtain, at the end of the second step, mixtures of tetracarbonyl compounds of the formulae (1) and (2) with minor proportions of tetracarbonyl compounds of the formula (4).

The conversion of the diacyl compounds to tetracarbonyl compounds may be carried out by any method known in organic chemistry to synthesize a carbonyl group from a methyl or methylene radical of one of these radicals containing one halogen (chlorine or bromine) or one of these radicals containing two halogens (preferably chlorine or bromine). These well-known techniques are described in the examples in greater details.

The m-terphenyl tetracarbonyl compounds according to the invention are monomers for manufacturing heterocyclic thermostable polymers. The latter mainly consist of recurrent units of the general formula:

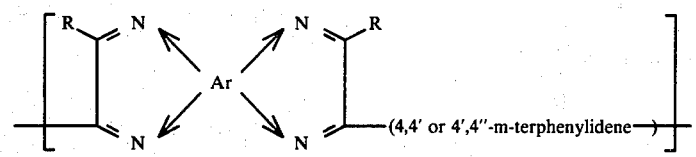
(12)

where the arrows indicate possible isomerism and each radical Ar is a tetravelnt aromatic radical containing one or more homocyclic or heterocyclic aromatic rings, the four valences of which are located on distinct carbon atoms and localized by pairs on adjacent carbon atoms of a given ring, i.e. in ortho position with respect to one another. The Ar radical comprises one or more rings, for example 2 to 6 rings, either coupled or joined, each of these rings preferably comprising from 5 to 7 atoms whose part may consist of oxygen, sulfur and/or nitrogen atoms.

When the radicals Ar contain several joined rings, the junction elements are, for example, a direct bond or one of the following atoms and groups:

$$-O-; \quad -S-; \quad -SO-; \quad -SO_2-; \quad -CO-; \quad -CHOH-;$$

$$-CH_2-; \quad -CF_2-; \quad -CO-NH-; \quad -\underset{R_2}{\overset{R_1}{\underset{|}{\overset{|}{C}}}}- ; \quad -\underset{R_2}{\overset{R_1}{\underset{|}{\overset{|}{S_1}}}}- ; \quad -\underset{CF_3}{\overset{CF_3}{\underset{|}{\overset{|}{C}}}}- ;$$

in which $R_1$ and $R_2$ are monovalent hydrocarbon groups such as, for example, alkyl, cycloalkyl or aryl radicals.

The R radical has the same meaning as given hereinbefore, the group shown as −(4,4' or 4',4''-m-terphenylidene)− represents the divalent aromatic m-terphenyl radical either in 4 and 4' positions or in 4' and 4'' positions.

These heterocyclic polymers having usually a polycondensation degree of from about 10 to several thousands and an inherent viscosity of from 0.6 to 3 dl/g, as measured at 30° C. with solutions containing 0.4 g of polymer per 100 ml of m-cresol.

They are manufactured by reacting at least one aromatic tetra-amine of the general formula:

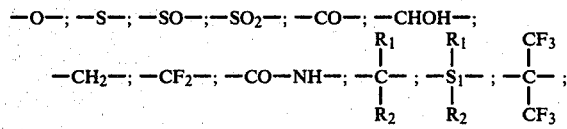
(13)

in which Ar is defined as above, with a substantially equimolecular amount of at least one of the m-terphenyl polyfunctional compounds of the formulae (1) and (2).

If the compounds of the formulae (1) and (2) are admixed with a small amount of compounds of the formulae (3), (4) and (5), a portion of the recurring units of the heterocyclic polymer (12) will contain 4,4''-ortho-terphenylidene, 4,4''-meta-terphenylidene and/or 4,4''-para-terphenylidene groups.

Synthesis of the polymers according to the invention may be carried out either by melting of the reactants, at for example, 100°–400° C., or in solution in an organic solvent, for example: phenol, m-cresol, cresylic acids, chlorophenols, dioxane, pyridine, dimethylformamide, dimethylacetamide, N-methylpyrrolidone, tetramethylensulfone, hexamethylphosphotriamide, chloroform, 1,2-dichloroethane or tetrachlorethane, at a moderate temperature, for example −20° to +250° C.

By way of example, the following tetra-amines can be used according to the invention: 1,2,4,5-tetra-amino-benzene, 2,3,6,7-tetra-amino-naphthalene, 2,3,5,6-tetra-amino-pyridine, 2,3,5,6-tetra-amino-pyrazine, 3,3'-diamino-benzidine, bis-(3,4-diamino-phenyl)ether, bis-(3,4-diamino-phenyl)methane, bis-(3,4-diamino-phenyl) ketone, bis-(3,4-diamino-phenyl) sulfide, bis-(3,4-diamino-phenyl)sulfone, 3,3',4,4'-tetra-amino-benzhydrol, 3,3',4,4'-tetra-amino-benzanilide, 3,3',4,4'-tetra-amino-diphenyl-dimethyl-silane, bis-(3',4'-diamino-4-phenoxy-phenyl)ether and 1,3-bis-(3,4-diamino-phenoxy)benzene.

As examples of m-terphenyl tetracarbonyl compounds within the scope of the invention, we will mention: 4,4'-bis-glyoxalyl-m-terphenyl, 4'-4''-bis-glyoxalyl-m-terphenyl, 4,4'-bis-methylglyoxaloyl-m-terphenyl, 4',4''-bis-methylglyoxalyl-m-terphenyl, 4,4'-bis-phenylglyoxaloyl m-terphenyl and 4',4''-bis-phenylglyoxaloyl-m-terphenyl, 4,4''-bis-glyoxalyl-m-terphenyl, 4,4''-bis-glyoxalyl-O.terphenyl, 4,4''-bis-glyoxalyl-p-terphenyl, 4,4''-bis-phenyl-glyoxaloyl-m-terphenyl, 4,4''-bis-phenyl-glyoxaloyl-O-terphenyl and 4,4''-bis-phenylglyoxaloyl-p-terphenyl may be present in minor proportions in admixture with said compounds.

For specific applications, it may be advantageous to prepare copolymers by admixing the above reactants with known reactants, for example, meta and para-diglyoxalyl benzenes, meta and para-bis-phenylglyoxaloyl-benzenes or bis(4-phenyl-glyoxaloyl-phenyl) ether.

The heterocyclic thermostable polymers, as above defined, have an increased solubility in organic solvents and are useful in a number of practical applications, such as the manufacture of composite materials, films, fibers, shaped articles, adhesives, insulating varnishes or coatings having a good resistance to heat and oxidation above 300° C.

The invention will be described in greater detail in the following specific examples, the details being given for illustration and not limitation. In these examples, the inherent viscosity of the polymers, expressed in dl/g, has been determined in 30° C. at a concentration by weight of 0.4 g of polymer per 100 ml of the selected solvent. The thermogravimetric analysis has been conducted with a thermobalance programmed at a 60° C. temperature increase per hour. Example 2 is given for comparison.

EXAMPLE 1

4'-acetyl m-terphenyl 280 g of acetyl chloride is added within 30 minutes to a suspension of 470 g of anhydrous aluminum chloride in 1.5 liter of methylene chloride cooled to a temperature from −25° to −15° C. The resulting complex dissolves in the solvent and a solution of 700 g of m-terphenyl in 2 liters of methylene chloride is then added within about 1 hour, while maintaining the temperature below −10° C. The reaction mixture is maintained at this temperature for 4 hours and at room temperature for one night. It is then hydrolyzed with 4 kg of ice and 1 liter of concentrated hydrochloric acid. A white precipitate, an organic phase and an aqueous phase are formed.

The precipitate which amounts to 42 g, is 4,4″-diacetyl p-terphenyl resulting from the acetylation of p-terphenyl formed by isomerization of m-terphenyl in the presence of aluminum chloride.

The organic phase is washed successively with water, a 10% aqueous solution of sodium carbonate and again water up to neutrality. After evaporation of methylene chloride, 750 g of raw product is separated. The mixture by distillation under vacuum gives: 82 g of m-terphenyl, 560 g of 4′-acetyl m-terphenyl, 15 g of 4,4″-diacetyl m-terphenyl and 50 g of distillation residue. It is clear that the major component is 4′-acetyl m-terphenyl.

EXAMPLE 2 (for comparison)

4-acetyl m-terphenyl 207 g of aluminum chloride and 300 g of m-terphenyl are successively dissolved into 2 liters of nitrobenzene. 102 g of acetyl chloride is added stepwise, while maintaining the temperature below 20° C. After 1 hour reaction at room temperature, the reaction mixture is heated to 45° C. for 5 hours. The mixture, once cooled, is hydrolyzed by means of 2 kg of ice and 500 ml of concentrated HCl.

Nitrobenzene is stripped with steam and the solid residue is dissolved into acetone. After filtration and the acetone evaporation, 400 g of crude product is obtained.

The following fractions are separated by vacuum distillation: 25 g of m-terphenyl, 54 g of 4′-acetyl m-terphenyl, 236 g of 4-acetyl m-terphenyl and 20 g of 4,4″-diacetyl p-terphenyl.

The Friedel and Crafts reaction, when conducted under conventional conditions, results mainly in a m-terphenyl acetylated isomer other than 4′-acetyl m-terphenyl.

EXAMPLE 3 m-terphenyl di-acetylation

An acylation complex is prepared at −20° C. in the conditions of example 1, by adding 785 g of acetyl chloride to a suspension of 1,330 g of aluminum chloride in 5 liters of methylene chloride, 920 g of m-terphenyl in 3 liters of the same solvent is then added. The reaction takes place at −10° C. for 6 hours and at room temperature for one night. After hydrolysis and washing, 1,100 g of raw product is isolated. This mixture is distilled in vacuo and yields: 65 g of m-terphenyl, 58 g of 4′-acetyl m-terphenyl, 75 g of 4,4″-diacetyl p-terphenyl, 104 g of 4,4″-diacetyl m-terphenyl, 400 g of 4,4′ and 4′,4″-diacetyl m-terphenyl and 400 g of polymeric residues. The mixture of the 4,4′ and 4′,4″ isomers may be subjected to a separation by Gas-Chromatography.

EXAMPLE 4 m-terphenyl bis-chloracetylation 230 g of m-terphenyl is reacted at −10° C. in tetrachloroethane with a complex prepared with 325 g of aluminum chloride and 283 g of chloracetyl chloride. 370 g of crude product is isolated after the same treatment as in example 1. By extraction with ethanol we obtain 150 g of a mixture of 4,4′(4′,4″) and (4,4″)-bischloracetyl m-terphenyls and 200 g of polymers.

EXAMPLE 5 m-terphenyl bis-dichloracetylation

When operating with 23 g of m-terphenyl, 30 g of aluminum chloride and 36 g of dichloracetyl chloride, we obtain, in the conditions of example 4, 18 g of 4,4′(4′,4″) and (4,4″) bis-dichloracetyl m-terphenyls and 10 g of polymers.

EXAMPLE 6 m-terphenyl bis-phenacetylation

A complex is prepared by adding 480 g of phenacetyl chloride at −20° C. to 400 g of aluminum chloride suspended in 1.5 liter of methylene chloride. A solution of 230 g of m-terphenyl in 0.8 liter of the same solvent is then added within 30 minutes. After 1 hour of reaction at −10° C. and 6 hours at room temperature, the mixture, treated as in example 1, yields 75 g of 4′-phenacetyl m-terphenyl, 130 g of a mixture of 4,4′ (4,4″) and (4′,4″) bis-phenacetyl m-terphenyls and 250 g of polymers. The 4,4″ isomers may be separated from this mixture by successive fractionated crystallizations in methylene chloride or ethanol. The remaining mixture may be subjected to an analytical separation (Gas-Chromatography).

EXAMPLE 7

24.4 g of selenium oxide is introduced into 100 ml of dioxane containing 2 ml of water and 0.3 ml of concentrated hydrochloric acid. 31.4 g of the mixture of 4,4′ and (4′,4″) -diacetyl m-terphenyl, as prepared in example 3, is added to this mixture, which is heated to reflux for 10 hours. After cooling, selenium is separated by filtration. The solution is treated with active coal and percolated through an alumina column. Dioxane is distilled under reduced pressure. The solid residue amounting to 24 g is crystallized from a dioxane-water mixture. We thus obtain 18 g of a mixture of 4,4′ and (4′,4″) bis-glyoxalyl m-terphenyl, as a di-hydrate.

EXAMPLE 8

10 g of a mixture of 4,4′ and (4′,4″) bis-chloracetyl m-terphenyl with 100 ml of dimethylsulfoxide is heated to 100° C. for 1.5 hour. After cooling, the solution is poured into 500 ml of water and stirred for a few hours. The precipitate which is formed is washed several times with hot water, dried and crystallized from n-propanol. We obtain 5.4 g of a mixture of 4,4′ and (4′,4″) bis-glyoxalyl m-terphenyl.

EXAMPLE 9

Anhydrous sodium methylate is prepared by adding 12 g of a 50% suspension of sodium hydride in heavy oil to 200 ml of anhydrous methanol. When no more hydrogen evolves, we add to the mixture a solution of 22.6 g of the bis-dichloracetyl m-terphenyl mixture of example 5 in 150 ml of methanol. At the end of the addition, the mixture is stirred at room temperature for one night, then diluted with 300 ml of ethyl ether and poured into water. The excess of sodium methylate is neutralized with a 10% hydrochloric acid solution. The ether phase is separated, washed with water, dried on sodium sulfate and ether is evaporated under reduced pressure. The solid residue is treated for one night with a mixture of tetrahydrofuran (50 ml) and 48% sulfuric acid (50 ml). The precipitate consisting of a 4,4' (4,4") and (4',4") bis-glyoxalyl m-terphenyl mixture is separated by filtration and dried.

EXAMPLE 10

130 g of the mixture of 4,4' and (4',4") bis-phenacetyl m-terphenyl of example 6 and 560 ml of acetic anhydride is introduced into a 1 liter flask fit out with a reflux cooler. The mixture is heated to 140°-150° C. and 125 g of selenium oxide is added thereto. After 5 hours of reaction at this temperture, the hot solution is filtered to eliminate selenium metal. The cooled solution yields a precipitate which is separated by filtration, washed with ether and dried. The unrefined product weighing 110 g is crystallized out from acetic acid to yield 90 g of a 4,4'- and (4',4") bis-phenyl glyoxyloxyl m-terphenyl mixture. Pure isomers are obtained when starting from pure phenacetyl compounds.

EXAMPLE 11

8.57 g of 3,3'-diamino benzidine and 50 ml of deaerated m-cresol are introduced into a 200 ml flask fit out with a stirrer and fed with nitrogen. 14.415 g of bis-glyoxalyl m-terphenyl dihydrate, as prepared in example 7, diluted with 50 ml of m-cresol is added stepwise. After reaction for one hour at 25° C. and one hour at 100° C., the polymer has an inherent viscosity of 0.6 dl/g in m-cresol and a softening temperature of 230°-240° C.

An E-181 glass fabric of 20 × 70 cm is impregnated with this solution. The impregnation is conducted in three successive passages each followed with a drying step at 120°-140° C., for 15 minutes, 30 minutes and 1 hour respectively. The impregnated fabric is cut into 8 identical elements which are superimposed and pressed under 20 bars for 10 minutes at 250° C., 1 hour from 250° to 400° C. and 4 hours at 400° C. After cooling, the material is reheated in inert atmosphere for 48 hours at a temperature from 250° to 420° C.

The material obtained has a bending strength at break of 60 kg/mm$^2$ at 25° C., 50 kg/mm$^2$ after 100 hours at 325° C. in the air and 40 kg/mm$^2$ after 100 hours at 350° C. in the air.

EXAMPLE 12

2.968 g of the bis-phenylglyoxyloyl-m-terphenyl of example 10 is reacted in inert atmosphere with a suspension of 1.2856 g of 3,3'-diamino benzidine in 35 ml of m-cresol. After 18 hours of reaction at 25° C., the viscous solution of polymer is diluted with 15 ml of m-cresol. The inherent viscosity of the polymer is 2.5 dl/g.

The solution is used to spread a film on a glass sheet with a 0.9 mm filmograph. The solvent is evaporated in nitrogen atmosphere for 3 hours at a temperature from 80° to 130° C. and under vacuum at 130° C. also for 3 hours. The polymer film, when detached from its support, retains 11% by weight of solvent. The latter is eliminated by heating under vacuum at 250° C. for 2 hours. When subjected to traction tests, the film has the following mechanical properties: tensile strength at break: 12 kg/mm$^2$; traction modulus: 220 kg/mm$^2$; lengthening at break: 9.5%. The thermogravimetric analysis shows a decomposition level of about 550° C. in argon atmosphere and 500° C. in air. The loss of weight is only 20% at 700° C. (argon) and 40% at 700° C. (air).

The resistance of the polymer to oxidation is determined by isothermal thermogravimetric analysis in air at 425° C. The weight losses are 1% after 20 hours, 5% after 58 hours, 10% after 82 hours, 20% after 107 hours and 30% after 138 hours. These figures show an exceptionally high resistance to oxidation.

EXAMPLE 13

0.9891 g of the tetraketone of example 10 and 0.4605 g of bis-(3,4-diamino phenyl) ether are used to prepare a polyquinoxaline in the conditions of example 12. The resulting polymer has an inherent viscosity of 2.85 dl/g in m-cresol. The films prepared with this polymer have a tensile strength of 11 kg/mm$^2$, a modulus of 240 kg/mm$^2$ and a lengthening at break of 10%. The thermogravimetric analysis under argon and air shows that the decomposition levels are 520° and 480° C. respectively.

EXAMPLE 14

0.1382 g of tetra-amino-benzene and 0.4946 g of the tetraketone of example 10 are reacted for 24 hours in 20 ml of m-cresol in the conditions of example 12. The polymer, once separated by precipitation in methanol, has an inherent viscosity of 1.97 dl/g. Its decomposition temperature is about 540° C. under argon atmosphere and 500° C. in air.

EXAMPLE 15

4.95 g of the tetraketone of example 10 and 2.14 g of 3,3'-diamino benzidine are reacted in 60 ml of deaerated meta-cresol. After reaction for one hour at room temperature, the polymer is precipitated in 200 ml of methanol. It is washed several times with methanol and dried at 80° C. in vacuo. 6.3 g of polyquinoxaline is obtained, its inherent viscosity in m-cresol being 1.1 dl/g. This polymer is fully soluble in chloroform, dichlorethane, tetrachlorethane, o-dichlorobenzene, phenol, m-cresol, p-chlorophenol, m-chlorophenol, m-methoxyphenol, pyridine, concentrated sulfuric acid, trifluoracetic acid, perfluoro-alcohols and perfluoroketones.

A 20% by weight solution of the polymer in chloroform is prepared and used to impregnate an E 181 glass fabric without finish. After drying at 50° C. for 1 hour, the fabric retains 38% by weight of resin. It is cut into 8 identical elements which are superimposed and pressed at 250° C. under a pressure of 30 kg/cm$^2$. The temperature of the press is brought to 400° C., maintained at this value for 2 hours and then at 450° C. for 30 minutes. The resulting material has a density of 1.82 and a bending strength at break of 60 kg/mm$^2$.

EXAMPLE 16

The solution of the polymer of example 15 in chloroform is used to impregnate a strip of E-112 glass fabric and steel plates of 10 × 15 cm. The two plates are stuck to each other by interposing the impregnated fabric at 250° C. under a pressure of 15 kg/cm$^2$. After 1 hour at 250° C., 1 hour at 300° C. and 1 hour at 350° C., the shearing strength of the material is 150 kg/cm$^2$.

We claim:

1. A member selected from the group consisting of a 4,4'-disubstituted meta-terphenyl derivative of the formula:

a 4',4''-disubstituted meta-terphenyl derivative of the formula:

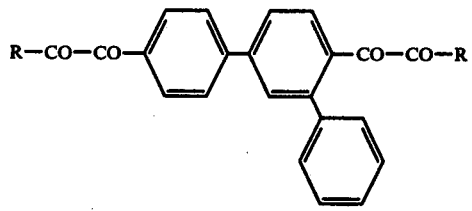

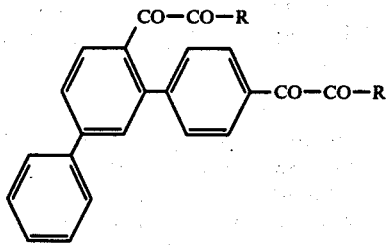

in which R is phenyl, and a mixture of both of said meta-terphenyl derivatives.

2. A composition consisting essentially of said mixture of meta-terphenyl derivatives, as defined in claim 1.

3. A composition consisting essentially of said mixture of both of said metal-terphenyl derivatives according to claim 1, and not more than a minor proportion of the 4,4''-disubstituted meta-terphenyl derivative of the formula

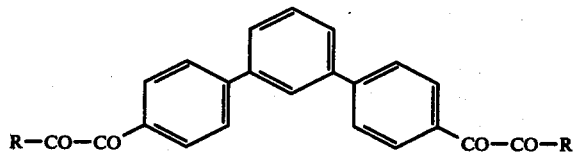

in which R is phenyl.

4. A composition according to claim 3, wherein the minor proportion of said 4,4''-disubstituted derivative does not exceed 30 molar %.